United States Patent [19]

Hammersmark et al.

[11] Patent Number: 5,429,617
[45] Date of Patent: Jul. 4, 1995

[54] RADIOPAQUE TIP MARKER FOR ALIGNMENT OF A CATHETER WITHIN A BODY

[75] Inventors: Dan J. Hammersmark; Kevin D. Taylor, both of Colorado Springs, Colo.; Steven R. Greenfield, Dallas, Tex.

[73] Assignee: The Spectranetics Corporation, Colorado Springs, Colo.

[21] Appl. No.: 165,300

[22] Filed: Dec. 13, 1993

[51] Int. Cl.⁶ .................................... A61M 5/00
[52] U.S. Cl. ........................ 604/264; 604/117; 604/282; 128/658
[58] Field of Search .......... 604/280, 263, 282, 117, 604/264; 128/657, 658

[56] References Cited

U.S. PATENT DOCUMENTS

| | | |
|---|---|---|
| Re. 33,569 | 4/1991 | Gifford, III et al. . |
| 4,669,469 | 6/1987 | Gifford, III et al. . |
| 4,781,186 | 11/1988 | Simpson et al. . |
| 4,844,062 | 7/1989 | Wells . |
| 4,848,336 | 7/1989 | Fox et al. . |
| 4,860,743 | 8/1989 | Abela . |
| 4,875,897 | 10/1989 | Lee . |
| 4,886,061 | 12/1989 | Fischell et al. . |
| 4,921,483 | 5/1990 | Wijay et al. . |
| 4,926,858 | 5/1990 | Gifford, III et al. . |
| 4,938,220 | 7/1990 | Mueller, Jr. ................ 128/658 |
| 4,968,306 | 11/1990 | Huss et al. . |
| 4,989,608 | 2/1991 | Ratner ..................... 128/658 X |
| 4,994,059 | 2/1991 | Kosa et al. . |
| 5,041,108 | 8/1991 | Fox et al. . |
| 5,041,109 | 8/1991 | Abela . |
| 5,047,040 | 9/1991 | Simpson et al. . |
| 5,053,044 | 10/1991 | Mueller et al. . |
| 5,090,959 | 2/1992 | Samson et al. . |
| 5,090,960 | 2/1992 | Don Michael . |
| 5,092,873 | 3/1992 | Simpson et al. . |
| 5,109,830 | 5/1992 | Cho . |
| 5,114,404 | 5/1992 | Clarke et al. . |
| 5,203,777 | 4/1993 | Lee ........................... 604/280 |
| 5,300,048 | 4/1994 | Drewes, Jr. et al. ......... 604/280 |

*Primary Examiner*—John D. Yasko
*Attorney, Agent, or Firm*—Cushman, Darby & Cushman

[57] ABSTRACT

A catheter having an outer wall of tubular shape, a cylindrical marker attached to the distal end of the catheter. The marker band includes markings for identifying the axial, rotational and yaw position of the catheter distal end when it is located in a body and viewed fluoroscopically.

37 Claims, 6 Drawing Sheets

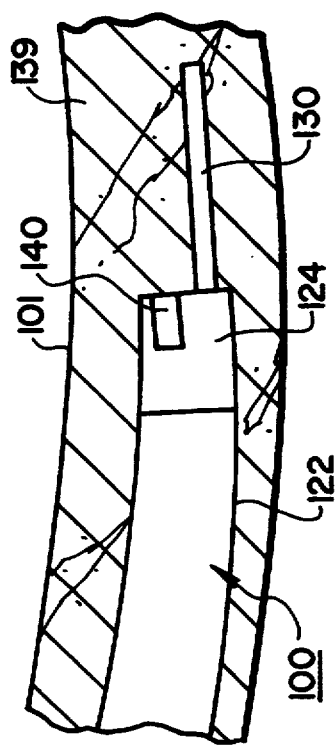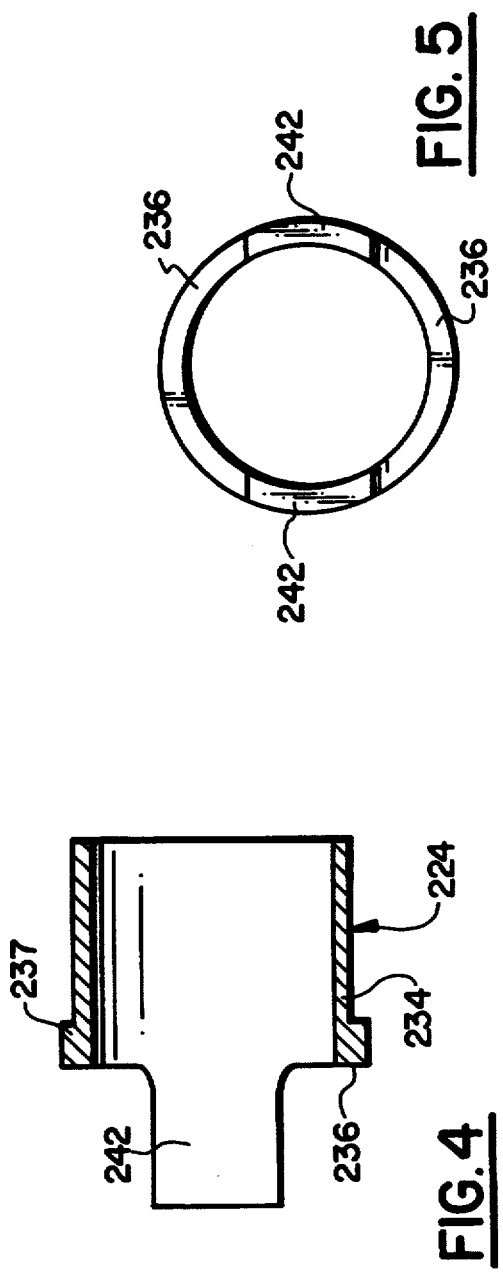

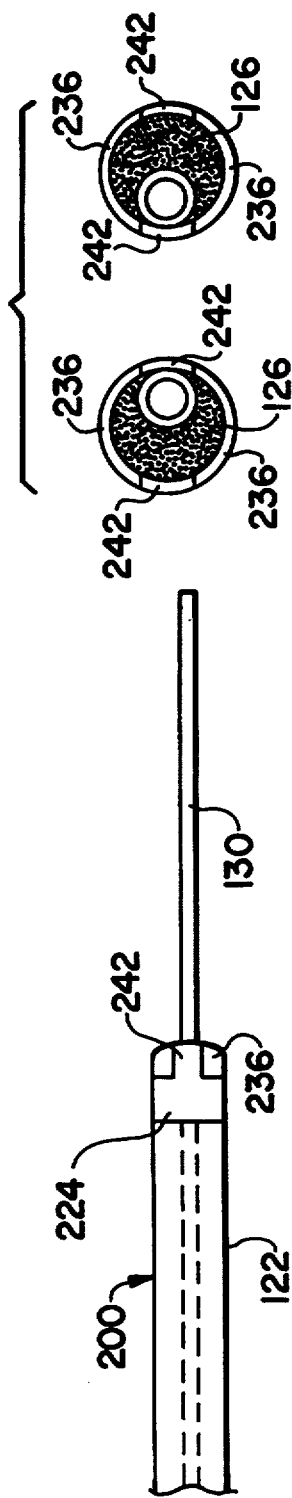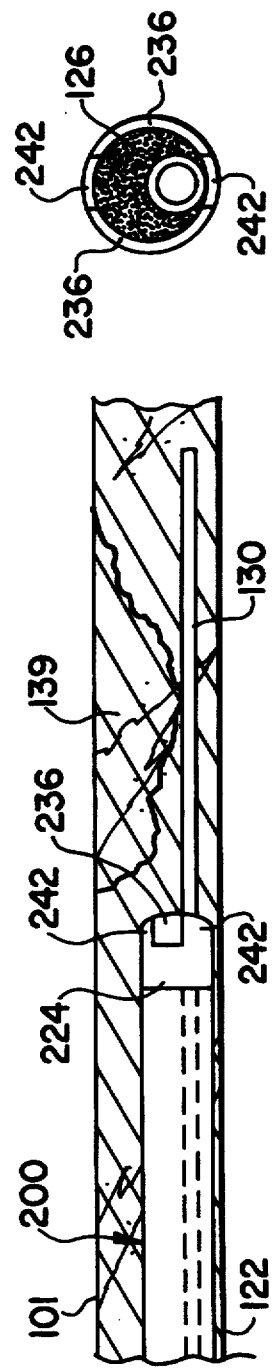

RADIOPAQUE TIP MARKER FOR ALIGNMENT OF A CATHETER WITHIN A BODY

BACKGROUND OF THE INVENTION

1. Field of the Invention

The present invention relates to catheters used within the body. In particular, the present invention relates to a radiopaque marker disposed at the distal end of a catheter for indicating the axial, rotational and yaw position of the distal end when viewed fluoroscopically within the body.

2. Description of the Art

Radiopaque markers are commonly placed on catheters to enhance a physician's ability to view the position of the catheter within bodily vessels or cavities. Circumstances may exist which require a physician to ascertain and improve alignment of the catheter tip after it is advanced in the body. A radiopaque marker provided at a catheter distal end, when viewed fluoroscopically, can enhance a physician's efforts and abilities.

U.S. Pat. No. 4,968,306 to Huss et al. (hereinafter "Huss") shows one conventional manner of marking a catheter distal end. Huss teaches a radiopaque marker band or ring which extends around the catheter near the distal end. The Huss configuration provides a physician the ability to visualize the catheter distal end's general axial location while the catheter is inside a patient's body.

Marking the catheter distal end in the manner as used in Huss does not reveal the precise axial location of the distal tip within a patient's body because the marker is not at the distal tip of the catheter. Moreover, it does not indicate the rotational position of the catheter's distal end.

Both U.S. Pat. No. 4,860,743 and U.S. Pat. No. 5,041,109, both to Abela, show a laser catheter having an end cap made from heat conducting material such as steel. Channels containing optical fibers run through the catheter tip and terminate at a spherical microlens. The channels are symmetrically disposed about the longitudinal axis of the tip. When fluoroscopically viewed the catheter tip will not present a substantially different image profile than a solid tip. Furthermore, the symmetrical shape of the tip does not aid a physician to determine the rotational orientation of the catheter tip.

U.S. Pat. Nos. 5,041,108 and 4,848,336 to Fox et al. (hereinafter "the Fox Patents") show placement of small radiopaque strips of predetermined size positioned on the catheter outer sheath near the distal end. The radiopaque strips aid in determining the rotational and axial position of the catheter tip inside the patient. Both Fox Patents show asymmetrically-placed radiopaque strips on the catheter outer sheath extending in directions parallel with a catheter axis. The Fox Patent configurations require an additional production step of attaching the radiopaque strips to the outer surface of the catheter outer sheath because the strips are not an integral part of the catheter distal tip.

The Fox Patents do not teach how the radiopaque strips are attached to the catheter. It is unclear if the strips are glued to the catheter surface, embedded in the catheter outer sheath, or attached by another technique. If the strips are not attached to the catheter securely, the strips could detach from the catheter while within the body. Such a result could cause a serious complications.

In summation, the above mentioned markers reveal, fluoroscopically, the general axial location of a catheter distal end within a patient's body. The markers of the Fox Patents further reveal the catheter distal tip rotational position. A problem associated with the above radiopaque markers is that none of them reveal the yaw of the catheter distal tip within a patient's body in a manner easily understood when viewed fluoroscopically. Furthermore, it is unclear how the radiopaque markers of the above mentioned apparatus are attached to the catheter.

SUMMARY OF THE INVENTION

In view of the limitations and shortcomings of the aforementioned radiopaque markers, as well as other disadvantages not specifically mentioned above, it is apparent that there exists a need for a radiopaque marker located at a catheter distal end capable of revealing its axial, rotational and yaw position within a body, when viewed fluoroscopically, by a physician. Therefore, it is an object of this invention to provide a catheter distal end with such an ability.

It is a further object of the present invention to provide a catheter having a radiopaque marker about its distal end such that the radiopaque marker is securely attached and is an integral part of the catheter.

It is a further object of the present invention to provide a catheter distal portion with a radiopaque marker having an outer surface that is continuous with the catheter outer surface.

It is a further object of the present invention to provide a laser catheter for use in angioplasty which enables a physician to fluoroscopically view the distal tip of the catheter within a body and understand the three dimensional positioning of the distal tip in order to better aim optical energy emanating from the catheter.

These objects are achieved by providing a catheter having an outer wall of tubular shape. A cylindrical marker is attached to the distal portion of the outer wall. The cylindrical marker includes markings that allow a physician to determine the axial and rotational position of the distal end of the catheter inside the body when viewed fluoroscopically. The marker is made of a radiopaque material and has an outer surface that is continuous with the catheter outer surface.

The yaw position of the catheter distal end may also be determined. Also, the cylindrical marker may extend around at least 180 circumferential degrees of the catheter.

Optical fibers, lumens, or mechanical or electrical devices may be incorporated into a catheter having a radiopaque marker of the present invention so that the catheter can be used for a specific or multiple functions inside the body.

BRIEF DESCRIPTION OF THE DRAWINGS

Other objects, features, and characteristics of the present invention as well as methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures, and wherein:

FIG. 3 is a view illustrating the first embodiment inside a body cavity such as a blood vessel;

FIG. 4 is a side cross-sectional view of a radiopaque marker of a second embodiment according to the present invention;

FIG. 5 is an elevational end view of the distal end of the catheter of the second embodiment of the present invention, with optical fibers and inner member removed for clarity;

FIG. 6A illustrates how the second embodiment appears fluoroscopically in a first pair of positions;

FIG. 6B illustrates end view of the second embodiment in each of the first pair of positions;

FIG. 7A illustrates how the second embodiment appears fluoroscopically in a second position;

FIG. 7B illustrates an end view of the second embodiment in the second position;

DETAILED DESCRIPTION OF THE PRESENTLY PREFERRED EXEMPLARY EMBODIMENTS

Figure 2:
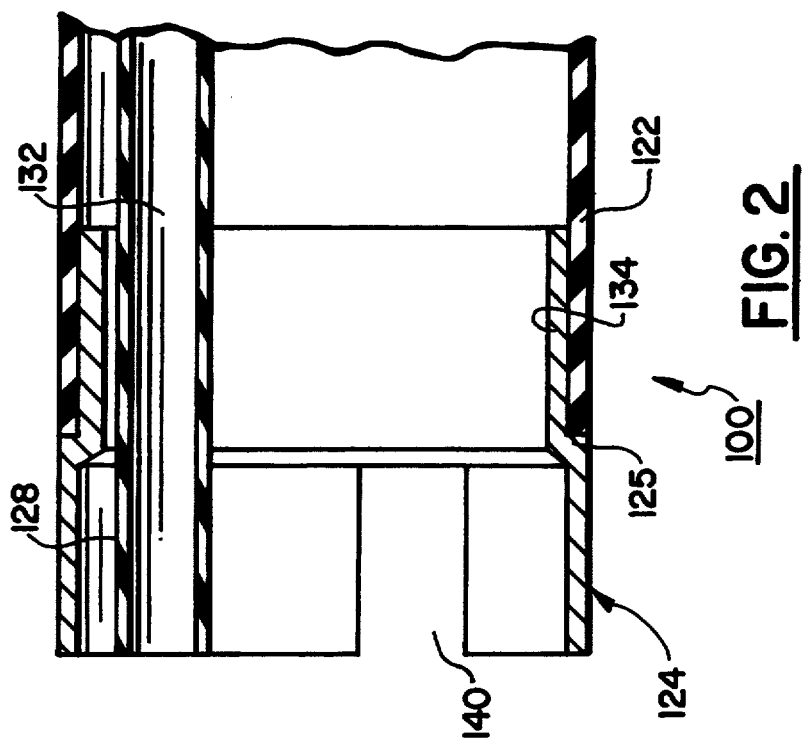
FIG. 2 is a longitudinal cross-sectional view of the first embodiment taken along 2—2 line of FIG. 1, with optical fibers removed for clarity.
Figure 1:
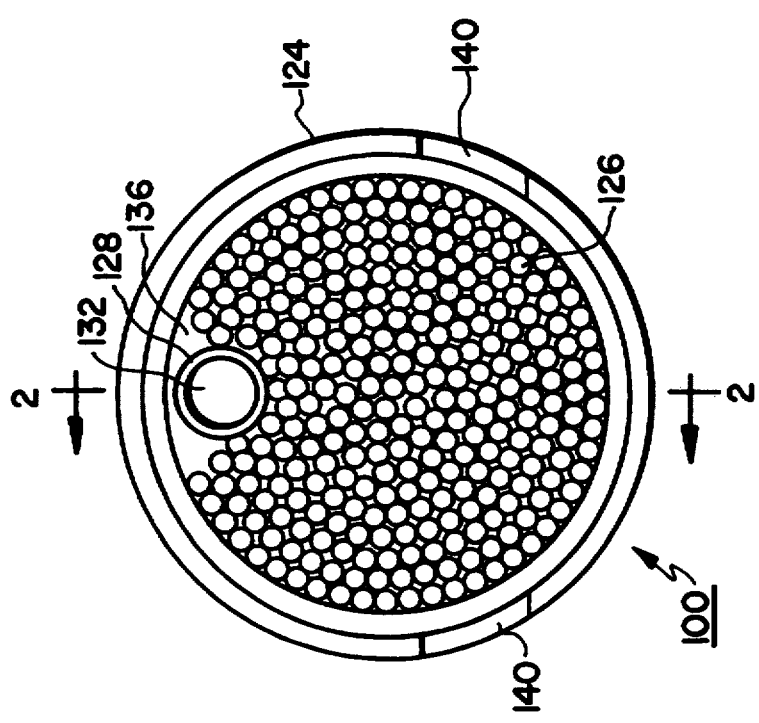
FIG. 1 is an end view of a first embodiment distal end of a catheter according to the present invention.

FIGS. 1, 2 and 3 illustrate details of a first exemplary embodiment of catheter 100. The catheter may be similar in structure to the illustrative structure disclosed in detail in U.S. patent application Ser. No. 07/857,458 filed Mar. 25, 1992, the contents of which are incorporated herein by reference.

The catheter 100 is of tubular shape having an outer wall 122 (FIGS. 2 and 3). A cylindrical marker 124 is affixed at the distal portion of the catheter 100. The cylindrical marker band 124 is ring shaped, extending for 360 circumferential degrees. However, marker band 124 does not need to complete a 360° circumference about the catheter distal end. Preferably, the band extends for at least 180 circumferential degrees around the catheter. The cylindrical marker is preferably made of a radiopaque material such as platinum, a platinum-iridium alloy or any other non-reactive material, such that when the catheter is disposed within a bodily cavity or vessel, the cylindrical marker band 124 can be visualized fluoroscopically by a physician or clinician performing a medical procedure on a patient.

Modern catheter uses require the catheter distal end to be specifically located at or near the point of interest within a body. For example, in laser angioplasty, wherein a catheter distal end emits optical energy to ablate occlusion or thrombosis 139 within vessel 101 as depicted in FIG. 3, it is important that the catheter distal end is aimed directly at the object of ablation. Vascular wall damage can result if the optical energy is inadvertently aimed incorrectly.

Catheter 100 contains optical fibers 126. The optical fibers have been removed from FIG. 2 for clarity. The optical fibers 126 carry optical energy to the distal tip of catheter 100. Inner member 128 is a jacket defining inner lumen 132. Inner member 128 extends longitudinally within the catheter 100. In FIG. 2, the inner member 128 is shown to end at the same place that the cylindrical marker band 124 ends. It is noted that the inner member 128 can extend beyond the distal end of the catheter 100. The inner member 128 can be used for a variety of functions, such as containing guide wire 130 (FIG. 3), or as a transportation structure for fluid within inner lumen 132.

Marker 124 of the first embodiment is attached to outer wall 122 via annular lip 134, which is overlapped by and bonded to the outer wall 122. The bonding may be accomplished via an adhesive glue, epoxy, ultrasonic weld or other medically accepted technique. Marker band 124 includes step 125, which outer wall 122 abuts. Within marker band 124, step 125 creates an area of greater diameter at the distal end of marker band 124. Optical fibers 126 extend longitudinally within outer wall 122 to the distal end of catheter 100. When catheter 100 is fabricated, filler 136 is wicked up the distal end of the catheter 100. Filler 136 can be an adhesive, such as epoxy. Filler 136, after being wicked, is interstitial with optical fibers 126. Cylindrical marker band 124 is held firmly to the distal portion of catheter 100 after filler 136 dries because filler 136 bonds to optical fibers 126 and fills the greater diameter area distally from step 125. Such a configuration ensures positive lock of marker band 124 in the axial direction to the catheter distal portion.

Two cut-away portions or slots 140 extend longitudinally from the distal end of the marker 126. The cut-away portions are approximately 150 circumferential degrees from each other. Although cut-away portion 140 is shown to be rectangular in shape, it is understood that the slots 140 can be any geometric shape and can extend circumferentially, longitudinally, diagonally, etc. in marker 124. The slot 140 can extend the full longitudinal length of the marker, provided the slot has a width of less that 180 circumferential degrees. It is also understood that there can be single, double or a multiplicity of slots incorporated into the marker band 124.

When the filler 136 is wicked up the distal portion of the catheter 100, the filler 136 fills the cut-away portions 140, further contributing to the positive lock of the marker 124 in the axial direction of the catheter 100.

When the marker of the first embodiment is viewed fluoroscopically within a bodily cavity or body vessel, its axial and rotational position can be determined. The axial position is determined via the position of the marker band distal end. The rotational position is determined based on the positions of the slots 140. Slots 140 become visible when they are rotationally aligned with the radiation.

As shown in FIG. 3, catheter 100 is disposed within blood vessel 101. It is desired to position catheter 100 so that fibers 126 (FIG. 1) irradiate occlusion 139. Guide wire 130 extends through inner lumen 132 beyond the distal tip of catheter 100. The alignment of catheter 100 can be determined by viewing blood vessel 101 fluoroscopically. When viewed in such a manner, marker 124 shows up as being a dark area as does the guide wire 130, while slots 140 show up as light areas when they are properly aligned.

FIGS. 4–7B depict a second embodiment of a radiopaque marker for a catheter distal portion according to the present invention (FIGS. 4 and 5) as well as drawings illustrating fluoroscopic views of catheter 200 (FIGS. 6A, 6B and 7A, 7B). The catheter to which the marker is attached can be the same as in the first embodiment. The radiopaque marker 224 is a forked band having two projections 242, spaced 180 circumferential degrees apart, which results in two enlarged grooved portions 236 from which projections 242 extend. Step portion 237 of marker band 224 is formed so as to abut against the end of outer wall 122 of catheter 200 when catheter 200 is fastened to marker band 224. That is, the outer wall of catheter 200 is exterior to annular lip 234 of marker 224.

Furthermore, filler used to secure fibers (not shown) holds the fibers to marker 224 and secures the fibers to catheter wall 122 as shown in FIG. 2. The filler is applied to complete a cylindrical annulus with projections 242. This helps to hold marker band 224 onto the catheter. The annular lip 234 may be attached to the outer wall 122 via an adhesive, glue, epoxy, ultrasonic weld or other medically acceptable technique.

The radiopaque marker of FIGS. 4 and 5, when viewed fluoroscopically, reveals the axial position of the catheter distal tip as shown in FIGS. 6A, 6B, 7A and 7B. Furthermore, the two extending portions 242 and two slots 236 fluoroscopically reveal the rotational position of the radiopaque marker when it is in the body. It is understood that each of the two slots need not be identical in size. That is, one slot may be narrower in the rotational direction or shorter in the axial direction than the other slot. When the slots are different sizes, the rotational position of marker band 224 is easier to determine fluoroscopically, assuming sufficient fluoroscopic resolution.

When the fluoroscopic view is that of FIG. 6A, two possible positions of marker 224 may exist as shown in FIG. 6B. When the fluoroscopic view is that of FIG. 7A, only one possible position of marker 224, and thus catheter 200, exists as shown in FIG. 7B.

Figure 8:
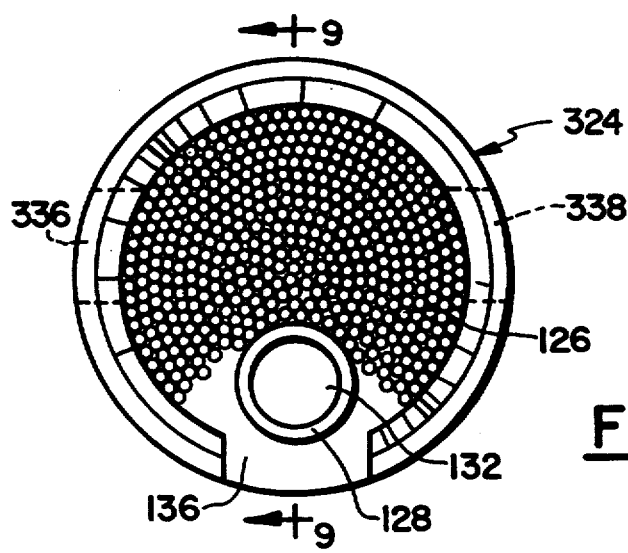
FIG. 8 is an elevational end view of the distal tip of a catheter according to a third embodiment, wherein the radiopaque marker has two holes to indicate position.
Figure 9:
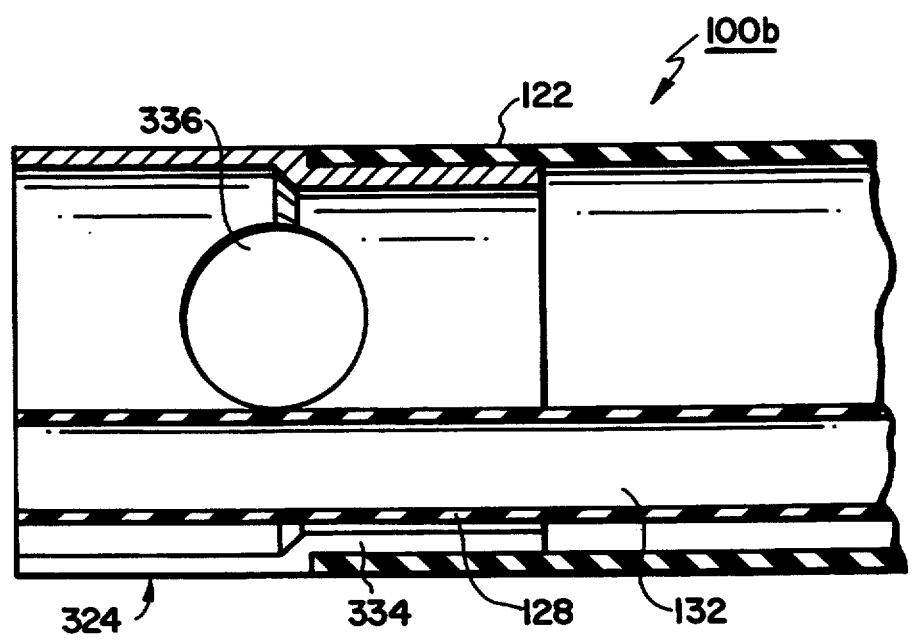
FIG. 9 is a side cross sectional view of the third embodiment taken along line 9—9 in FIG. 8 with optical fibers removed for clarity.
Figure 10:
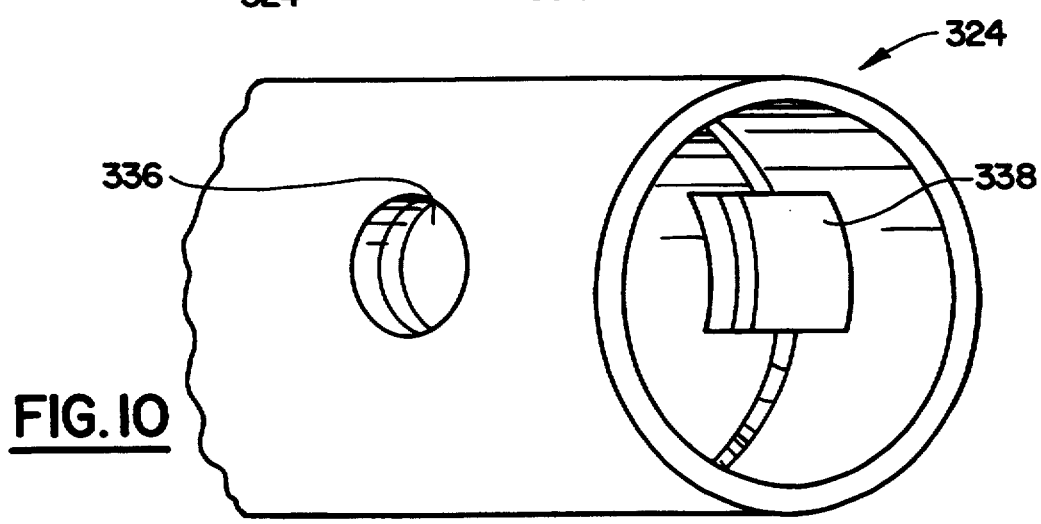
FIG. 10 is a perspective view of the marker band according to the third embodiment.

FIGS. 8 and 9 depict a third embodiment of the catheter distal portion with a marker band 324. Internal details of the catheter are shown in FIG. 8, with the optical fibers having been removed in FIG. 9 for clarity. FIG. 10 is a perspective view of marker band 324. This exemplary embodiment incorporates two holes 336 and 338 each extending through cylindrical marker 324, 180 circumferential degrees apart. Hole 338 may be larger than hole 336 or shaped differently as shown in FIG. 10.

The marker 324 extends beyond the distal end of the catheter outer wall 122 to the distal end of the catheter 300. Marker 324 is stepped so that annular lip fits inside catheter outer wall 122, with wall 122 abutting the "step" in marker band 324. Note in FIGS. 8 and 10 that marker 324 does not form a complete ring, but rather is open near inner lumen 132. Holes 336 and 338 enable the distal end axial position to be located fluoroscopically when inserted in the body, as well as revealing the rotational position of the catheter distal end when viewed fluoroscopically. The holes 336 and 338 may be circular holes of different diameters, which make the rotational position of the distal portion easy to determine. Furthermore, the centers of holes 336 and 338 share the same catheter axial plane making the yaw position of the catheter tip determinable when viewed fluoroscopically because of the alignment or misalignment of the hole centers. When the holes are shaped differently, as depicted in FIG. 10, it is possible to fluoroscopically identify which hole is closer to the X-ray receiver, thus uniquely determining the rotational position of catheter 300. When viewed fluoroscopically, the holes 336 and 338 appear transparent as compared to the remaining portions of marker 324.

Filler 136, after being wicked up the optical fibers 126, from the distal end of catheter 300, fills holes 336 and 338, and is interstitial with the optical fibers. Also, the filler fills the larger diameter distal portion of marker 324 beyond the step. Thus, the filler creates positive lock in the axial and rotational directions of the catheter when the filler cures. The positive lock prevents the marker 324 from detaching from the catheter distal portion. The filler further provides a continuous smooth outer surface on the marker band where the holes 336 and 338 are filled.

Figure 12:
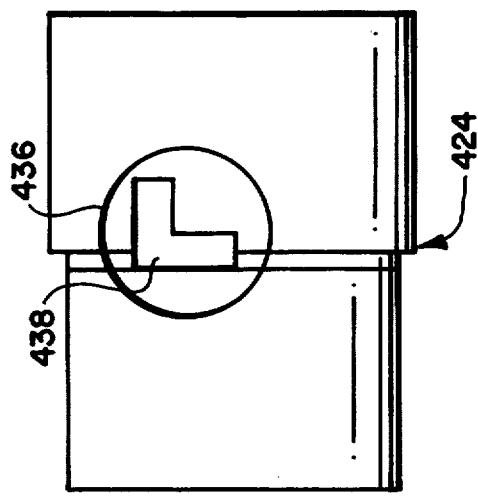
FIG. 12 is a side elevational view of the fourth embodiment.
Figure 11:
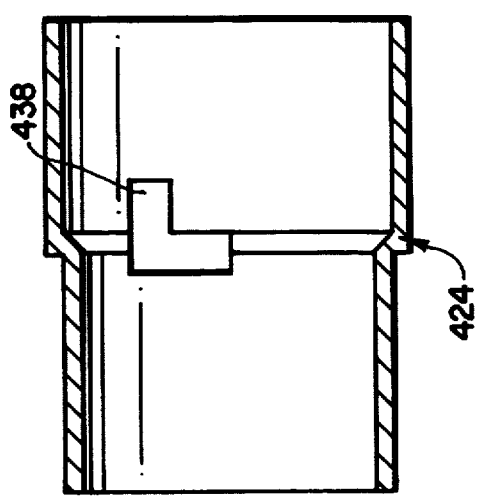
FIG. 11 is a cross-sectional view of a radiopaque marker according to a fourth embodiment.

FIGS. 11 and 12 depict a variation in the marker band of the third exemplary embodiment of the present invention. Instead of employing a circular and a square hole as in FIG. 10, a circular hole 436 and a character-shaped hole 438 are employed. In FIG. 11, character 438 is an "L". Use of the "L" enables the physician or clinician to determine the rotational position of catheter 400 due to the character's orientation. Note how the "L" in FIG. 11 is smaller than the circular hole on the opposite side of marker 424. In FIG. 12, "L" 438 is visible through hole 436, but the outline of hole 436 is not visible through "L" 438.

Figure 14:
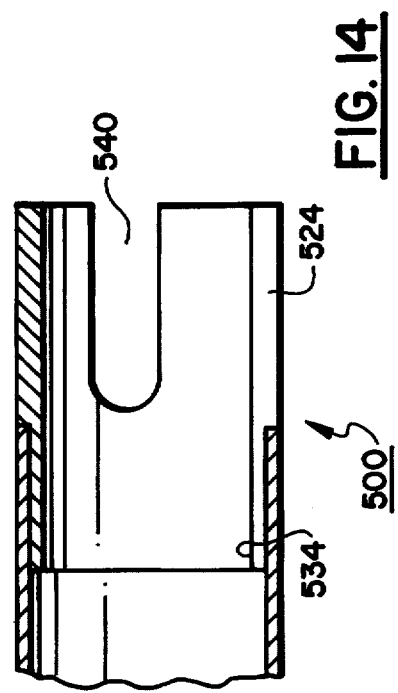
FIG. 14 is a cross-sectional view of the fifth embodiment taken along the line 14—14 line of FIG. 13, with optical fibers and inner lumen removed for clarity.
Figure 13:
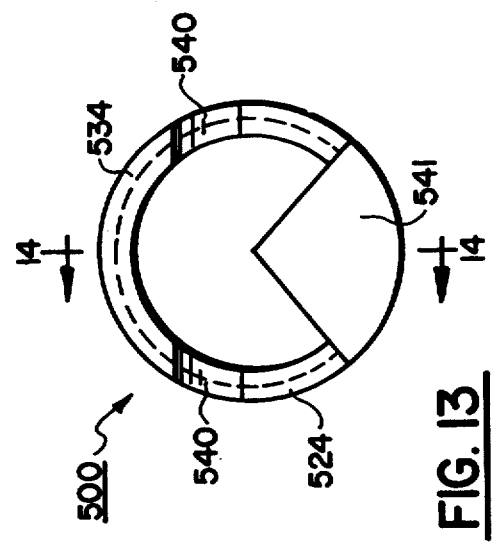
FIG. 13 is an end view of a fifth embodiment of the present invention, with optical fibers and inner member removed for clarity.

FIGS. 13 and 14 depict a fifth exemplary embodiment of the present invention in the same manner as the previous embodiments. Catheter 500 is equipped with a cylindrical marker 524 having an annular lip 534. Two slots 540 extend longitudinally from the distal end of the cylindrical marker 524. The two slots 540 do not extend the full longitudinal length of the marker 524. A third slot 541 extends the full longitudinal length of the marker 524. Slot 541 encompasses less than 180 circumferential degrees of the marker 524. As shown, slot 541 is 100 circumferential degrees in width. In the fifth embodiment, the inner wall of marker 524 is at a constant radius from the longitudinal axis rather than stepped. The stepped portion is not needed, as the adhesive used to bond the fibers with the marker fills groove 540, thus holding the fibers to the marker. This holds true with respect to all earlier embodiments, in that the presence of holes or slots makes the step portion inessential to the fastening of the marker band to the catheter.

In this fifth embodiment, like the previous embodiments, the combination of marker band and slots allow a physician or attending clinician to determine the axial, rotational and yaw position of the catheter distal end inside a bodily vessel when the catheter distal end is viewed fluoroscopically. Furthermore, slots 540, in combination with the wicked filler as described in earlier preferred exemplary embodiments, create a positive lock in the axial direction so that the marker 524 does not detach from the distal portion of the catheter while in the body. The filler is shaped and buffed to form a continuous smooth surface with the outer wall of the marker band.

Figure 15:
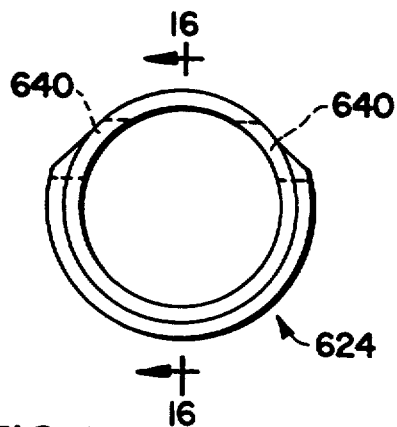
FIG. 15 is an end view of the distal end of a catheter according to a sixth embodiment of the present invention, with internal structures removed for clarity.
Figure 16:
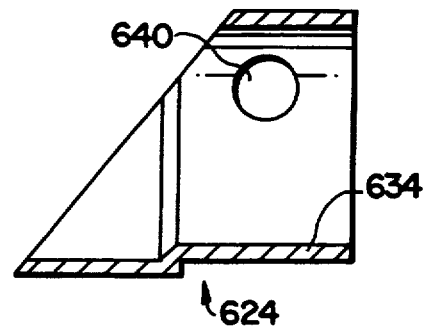
FIG. 16 is a cross-sectional view of the marker band of the sixth embodiment taken along the line 16—16 in FIG. 15.
Figure 17:
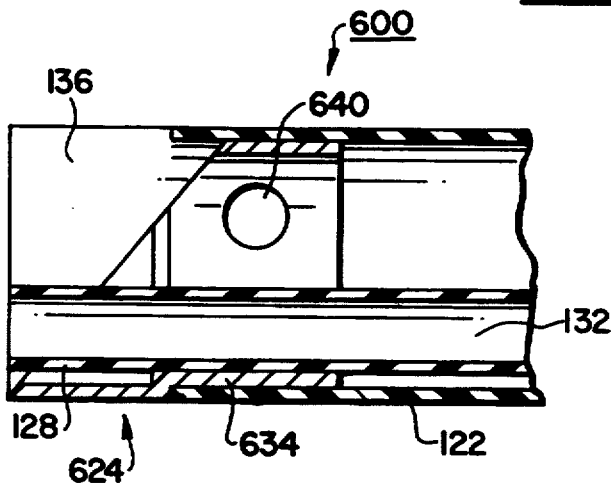
FIG. 17 is a cross-sectional view of the catheter of the sixth embodiment with optical fibers removed for clarity.

A sixth preferred exemplary embodiment of the present invention is depicted in FIGS. 15, 16, and 17 as the distal portion of catheter 600. Here the marker 624 is attached to the outer wall 122 using the annular lip 634 as in the other exemplary embodiments described above. FIGS. 15-17 depict the distal edge of marker 624 as being angled with respect to a plane perpendicular to the longitudinal axis of the catheter 600. Grooves, notches, slots or holes can be added to the marker of the sixth embodiment, as described in the first through fifth exemplary embodiments, to further aid the fluoroscopic viewing of the axial, rotational and yaw position of the catheter distal end. Circular holes 640 are shown in FIGS. 15-17.

As shown in FIG. 17, outer catheter wall 122 abuts the stepped portion of marker 624. Inner annular lip 634 is secured to the interior surface of outer catheter wall 122. Second lumen wall 128 defines inner lumen 132 so that the inner lumen does not obscure holes 640.

Filler 136 fills the area where the distal portion of the catheter 600 is not encased by the marker 624. The filler 136 is also interstitial with the optical fibers (not shown), which extend to the catheter distal end. Thus, filler 136 fills distally expanded portion of marker band 624 beyond the step. As a result, the filler 136 establishes positive lock in the axial direction of the catheter which holds the cylindrical marker 624 firmly in place.

Figure 18:
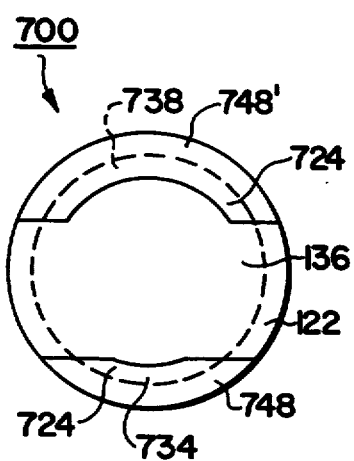
FIG. 18 is an end view of a catheter of a seventh embodiment of the present invention, with optical fibers removed for clarity.
Figure 19:
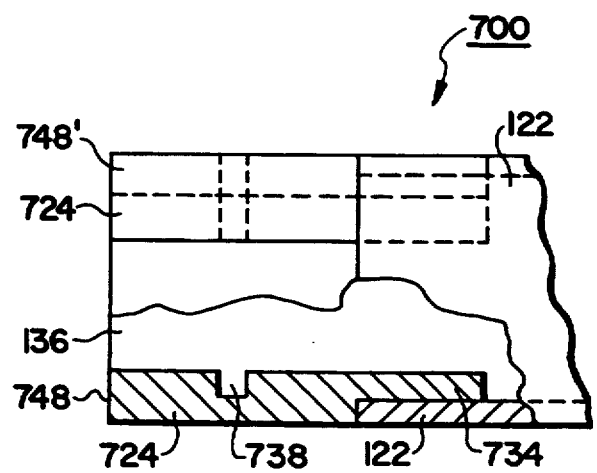
FIG. 19 is a cut-away side elevational view of the seventh embodiment of the present invention, with internal structures removed for clarity.

A seventh preferred exemplary embodiment of the present invention is depicted in FIGS. 18 and 19 as distal portion of catheter 700. Here, the marker 724 enables the distal end, axial and rotational position to be located fluoroscopically when inserted in the body. Marker band 724 is divided into two strips 748 and 748'. The circumferential width of strip 748 is narrower than the circumferential width of 748'. Both strips 748 and 748' extend in the distal direction beyond the end of the outer wall 122. Of course, the outer wall 122 can extend to the distal end of the catheter where the strips 748 and 748' are not present. An annular groove 738 extends annularly about the inner perimeter of the marker 724. Optical fibers (not shown) extend longitudinally inside the distal portion of catheter 700. Filler 136 is wicked up the distal portion of distal portion of catheter. The filler 136, after the wicking processes, is interstitial with the optical fibers and fills the annular groove 738. The cylindrical marker 724 is held firmly in place after the filler 136 cures because the filler 136 bonds to the optical fibers and conforms to the annular groove and, thus, provides positive lock on the marker 724 in the axial direction. It should be understood that the filler 136 also fills the space between strips 748 and 748' such that the outer surface of the distal portion is smooth and continuous. The outer surface is also smooth and continuous where the strips 748 and 748' meet the outer wall 122.

A lip 734 is overlapped by the outer wall 122. The lip 134 can be attached to the outer wall 122 by way of epoxy, glue, ultrasonic weld or any other medically accepted method.

The strips 748 and 748' can be viewed fluoroscopically, revealing the axial position of the distal portion of catheter 700. Since the sizes of the strips 748 and 748' are different, the rotational position of the distal portion can be determined. Furthermore, the yaw of the catheter distal end can be determined based on an offset shadow created about the annular groove 738 when the catheter distal portion is viewed fluoroscopically. Furthermore, as explained earlier, a small groove or hole of alphanumeric or geometric shape can be placed on one of the strips 748 to aid in the fluoroscopic determination of the catheter yaw.

Marker 724 can be comprised of a plurality of radiopaque strips 748. The strips can be a variety of shapes and orientations. One of ordinary skill in the art could prescribe other useful shapes that would enable the axial, rotational and yaw position to be visualized when the catheter distal portion is viewed fluoroscopically.

The radiopaque marker of the present invention can be used in a variety of medical treatments. Such treatments include, but are not limited to, laser and balloon angioplasty, laparoscopic, and endoscopic techniques. The marker enhances a physician's or clinician's ability to envision the exact location, position and pointing direction of the catheter distal end when it is inside a body and viewed fluoroscopically.

Of course, a variety of clinical devices besides a fluoroscope can be used to view small radiopaque objects inside a body. The radiopaque marker of the present invention can be viewed by any such a device.

A person of ordinary skill in the art would understand and appreciate the multitude of variations with respect to markings placed on a radiopaque marker to aid the determination of catheter distal end axial, rotational and yaw position within the body when viewed fluoroscopically. Slots, holes, notches, grooves, alphanumeric, parabolic shapes, geometric shapes, etc. can all be used as markings on the radiopaque marker. For example, the part of marker band disposed towards the distal tip of the catheter away from the abutment of the outer catheter wall with the stepped portion of the marker band may have a groove therein, while the part of the marker band nearest the proximal end of the catheter has a hole therein. Although a few preferred exemplary embodiments of the present invention have been shown and described, it will be appreciated by those skilled in the art that changes may be made in the disclosed embodiments without departing from the principles and spirit of the invention, the scope of which is defined in the appended claims.

What is claimed is:

1. A catheter comprising:
   a tubular outer wall having a longitudinal axis;
   a cylindrical marker attached to a distal portion of the outer wall, the marker including means for identifying axial and rotational positions of the distal portion when the distal portion is inserted in a body, the marker being made from a radiopaque material;
   at least one optical fiber disposed parallel with the longitudinal axis of the outer wall and within the outer wall; and means for providing a positive lock of the marker to the catheter in the axial direction.

2. The catheter of claim 1, wherein the identifying means includes a hole extending through the marker.

3. The catheter of claim 2, wherein the hole is of a geometric shape being asymmetric with respect to a longitudinal axis of the outer wall.

4. The catheter of claim 2, wherein the hole is of alphanumeric shape.

5. The catheter of claim 1, wherein the identifying means comprises a notch disposed on the marker.

6. The catheter of claim 1, wherein said cylindrical marker is formed as an annulus.

7. The catheter of claim 1, further comprising a groove disposed on the extending portion of the identifying means.

8. The catheter of claim 7, wherein the groove is of alphanumeric shape.

9. The catheter of claim 1, wherein the identifying means includes a slot extending the entire longitudinal length of the marker, the slot width being less than 180 circumferential degrees of the marker.

10. The catheter of claim 1, wherein the identifying means comprises a slot.

11. The catheter of claim 10, wherein the slot extends less than 180 circumferential degrees about the marker.

12. The catheter of claim 1, wherein an outer surface of the marker is continuous with an outer surface of the outer wall.

13. The catheter of claim 1, wherein the identifying means outer surface is continuous with the outer wall outer surface.

14. The catheter of claim 1, further comprising an inner member of annular shape disposed at least within the distal portion, extending longitudinally parallel with the outer wall longitudinal axis, and within the outer wall.

15. The catheter of claim 1, wherein the means for identifying further identifies a yaw position of the distal portion when the distal portion is inserted in a body.

16. The catheter of claim 1, wherein the marker includes an annular lip about the marker band proximal edge overlapped by the distal portion of the outer wall.

17. The catheter of claim 1, wherein the means for providing positive lock includes a notch located on the cylindrical marker inner surface.

18. The catheter of claim 17, wherein the means for providing positive lock includes a filler being interstitial with the optical fibers and disposed within the notch.

19. The catheter of claim 1, wherein the providing means includes adhesive disposed within the outer wall and being an integral part of the distal portion outer surface.

20. The catheter of claim 2, wherein the providing means includes an adhesive interstitial with the optical fibers and being an integral part of the distal portion outer surface.

21. The catheter of claim 1, wherein the means for identifying is asymmetrical about a longitudinal axis when viewed from a location perpendicular to the catheter longitudinal axis.

22. A catheter comprising:
a tubular outer wall;
a cylindrical marker contiguous to and extending in a distal direction beyond a distal end of the outer wall, the marker having a predetermined shape and extending in a longitudinal direction toward a distal end of the catheter, the marker including a means for identifying axial and rotational positions of a distal portion of the catheter when the distal portion is inserted in a body;
a plurality of optical fibers disposed within the outer wall parallel to an outer wall longitudinal axis, the optical fibers extending to a distal end of the catheter; and
means, in combination with the identifying means, for providing positive lock of the marker to the catheter in the axial direction.

23. The catheter of claim 22, wherein the providing means is interstitial with the optical fibers and engaged with the identifying means.

24. The catheter of claim 1, wherein the providing means is an integral part of an outer surface of the distal portion.

25. The catheter of claim 22, wherein the outer surface of the distal portion of the catheter is continuous with an outer surface of the outer wall.

26. The catheter of claim 22, wherein the identifying means comprises a portion of radiopaque material extending parallel to a longitudinal axis of the outer wall and of predetermined shape aligned with the outer wall.

27. The catheter of claim 22, wherein the identifying means includes a hole extending through the marker.

28. The catheter of claim 22, wherein the identifying means includes an alphanumeric shape.

29. The catheter of claim 22, wherein the identifying means comprises an annular notch disposed on an inner circumferential surface of the marker.

30. The catheter of claim 22, wherein the identifying means comprises a groove disposed on an inner circumferential surface of the marker.

31. The catheter of claim 22, wherein the identifying means includes a slot extending from the catheter distal end longitudinally along a longitudinal portion of the marker, the slot being of predetermined shape.

32. The catheter of claim 31, wherein the slot extends the full longitudinal length of the marker, the slot's width being less than 180 circumferential degrees about the marker.

33. The catheter of claim 22, wherein the identifying means includes a plurality of radiopaque strips having a geometric shape extending in the distal direction.

34. The catheter of claim 33, wherein at least one of the strips is a different size than the other strips.

35. The catheter of claim 22, wherein the identifying means includes a marker distal tip having edges extending in a proximal direction and angled with respect to a catheter longitudinal axis.

36. The catheter of claim 22, wherein the identifying means further includes a means for identifying yaw of the catheter distal end when the distal portion is inserted in a body.

37. A catheter comprising:
an outer wall of tubular shape;
a cylindrical marker made from a radiopaque material and attached to a distal portion of the outer wall, the marker including means for identifying axial and rotational positions of the distal portion when the distal portion is inserted in a body, the identifying means comprising a portion of radiopaque material being of predetermined shape in alignment with the outer wall and extending parallel to a longitudinal axis of the outer wall, the radiopaque material portion extending from a distal side of the marker;

a plurality of optical fibers disposed within the outer wall and parallel with the longitudinal axis of the outer wall; and means for positionally fixing the marker to the catheter in the axial direction, the providing means including an adhesive interstitial with the optical fibers and an integral part of the distal portion outer surface.

* * * * *